(12) United States Patent
Zones et al.

(10) Patent No.: US 7,432,402 B2
(45) Date of Patent: Oct. 7, 2008

(54) PARTIAL OXIDATION USING MOLECULAR SIEVE SSZ-74

(75) Inventors: Stacey I. Zones, San Francisco, CA (US); Allen W. Burton, Jr., Richmond, CA (US)

(73) Assignee: Chevron U.S.A., San Ramon, CA (US)

( * ) Notice: Subject to any disclaimer, the term of this patent is extended or adjusted under 35 U.S.C. 154(b) by 0 days.

(21) Appl. No.: 11/614,695

(22) Filed: Dec. 21, 2006

(65) Prior Publication Data

US 2007/0149789 A1 Jun. 28, 2007

Related U.S. Application Data

(60) Provisional application No. 60/754,811, filed on Dec. 28, 2005.

(51) Int. Cl.
| | |
|---|---|
| C07C 45/00 | (2006.01) |
| C07C 35/08 | (2006.01) |
| C07C 27/00 | (2006.01) |
| C07D 301/03 | (2006.01) |
| C07D 301/12 | (2006.01) |

(52) U.S. Cl. .................. 568/338; 568/836; 568/959; 549/523; 549/531

(58) Field of Classification Search ................ 568/338, 568/836, 959; 549/523, 531
See application file for complete search history.

(56) References Cited

U.S. PATENT DOCUMENTS 4,410,501 A   10/1983   Taramasso et al.
4,833,260 A  *  5/1989   Neri et al. .................. 549/531
4,910,006 A    3/1990   Zones et al.
5,316,753 A    5/1994   Nakagawa

OTHER PUBLICATIONS

Tatsumi, T. et al., Shape-selective oxidation of alkanes with hydrogen peroxide catalysed by titanosilicate, J. Chem. Soc., Chem. Commun, 1990(6), 476-477.*
U.S. Appl. No. 11/614,670, filed Dec. 21, 2006, entitled Molecular Sieve SSZ-74 Composition of Matter and Synthesis Thereof, 20 pages.
U.S. Appl. No. 11/614,683, filed Dec. 21, 2006, entitled Hydrocarbon Conversion Using Moleclar Sieve SSZ-74, 55 pages.
U.S. Appl. No. 11/614,688, filed Dec. 21, 2006, entitled Reduction of Oxides of Nitrogen in a Gas Stream Using Molecular Sieve SSZ-74, 18 pages.
U.S. Appl. No. 11/614,701, filed Dec. 21, 2006, entitled Acylation Using Molecular Sieve SSZ-74, 18 pages.
U.S. Appl. No. 11/614,706, filed Dec. 21, 2006, entitled Oxygenate Conversion Using Molecular Sieve SSZ-74, 19 pages.
U.S. Appl. No. 11/614,638, filed Dec. 21, 2006, entitled Gas Separation Using Molecular Sieve SSZ-74, 17 pages.
U.S. Appl. No. 11/614,714, filed Dec. 21, 2006, entitled Synthesis of Amines Using Molecular Sieve SSZ-74, 18 pages.
U.S. Appl. No. 11/614,720, filed Dec. 21, 2006, entitled Treatment of Engine Exhaust Using Molecular Sieve SSZ-74, 25 pages.

(Continued)

*Primary Examiner*—Yvonne Eyler
*Assistant Examiner*—Jennifer Y Cho
(74) *Attorney, Agent, or Firm*—Susan Abernathy; Richard Sheridan

(57) ABSTRACT

The present invention relates to new crystalline molecular sieve SSZ-74 prepared using a hexamethylene-1,6-bis-(N-methyl N-pyrrolidinium) dication as a structure-directing agent, and processes employing SSZ-74 in a catalyst.

6 Claims, 1 Drawing Sheet

OTHER PUBLICATIONS

U.S. Appl. No. 11/614,726, filed Dec. 21, 2006, entitled Beckmann Rearrangement Using Molecular Sieve SSZ-74, 22 pages.

D R.C. Huybrechts, et al., Oxyfunctionalization of alkanes with hydrogen peroxide on titanium silicalite, Letters To Nature, May 17, 1990, vol. 345, Laboratorium voor Oppervikatechemie, Katholieke Univeritelt Leuven, Kardinaal Mercienlaan 92, B-3030 Heverlee, Belgium.

Takashi Tatsumi et al., Shape-selective Oxidation of Alkanes with $H_2O_2$ catalysed by Titanosillcate, J. Chem. Soc. Chem. Commun. 1990, 476-477, Department of Synthetic Chemistry, Faculty of Engineering, The University of Tokyo, Hongo, Tokyo 113, Japan.

* cited by examiner

PARTIAL OXIDATION USING MOLECULAR SIEVE SSZ-74

This application claims the benefit under 35 USC 119 of Provisional Application No. 60/754,811 filed Dec. 28, 2005.

BACKGROUND OF THE INVENTION

1. Field of the Invention

The present invention relates to new crystalline molecular sieve SSZ-74, a method for preparing SSZ-74 using a hexamethylene-1,6-bis-(N-methyl-N-pyrrolidinium) dication as a structure directing agent ("SDA") and uses for SSZ-74

2. State of the Art

Because of their unique sieving characteristics, as well as their catalytic properties, crystalline molecular sieves and zeolites are especially useful in applications such as hydrocarbon conversion, gas drying and separation. Although many different crystalline molecular sieves have been disclosed, there is a continuing need for new molecular sieves with desirable properties for gas separation and drying, hydrocarbon and chemical conversions, and other applications. New molecular sieves may contain novel internal pore architectures, providing enhanced selectivities in these processes.

SUMMARY OF THE INVENTION

The present invention is directed to a family of crystalline molecular sieves with unique properties, referred to herein as "molecular sieve SSZ-74" or simply "SSZ-74".

In accordance with the present invention, there is provided a process for oxidation of hydrocarbons comprising contacting said hydrocarbon with an oxidizing agent in the presence of a catalytically effective amount of a titanium-containing molecular sieve for a time and at a temperature effective to oxidize said hydrocarbon, wherein the titanium-containing molecular sieve is a molecular sieve having a mole ratio greater than about 15 of (1) silicon oxide to (2) titanium oxide and having, after calcination, the X-ray diffraction lines of Table II.

There is further provided in accordance with this invention a process for epoxidation of an olefin comprising contacting said olefin with hydrogen peroxide in the presence of a catalytically effective amount of a titanium-containing molecular sieve for a time and at a temperature effective to epoxidize said olefin, wherein the titanium-containing molecular sieve is a molecular sieve having a mole ratio greater than about 15 of (1) silicon oxide to (2) titanium oxide and having, after calcination, the X-ray diffraction lines of Table II.

Further provided in accordance with the present invention is a process for oxidizing cyclohexane comprising contacting said cyclohexane with hydrogen peroxide in the presence of a catalytically effective amount of a titanium-containing molecular sieve for a time and at a temperature effective to oxidize said cyclohexane, wherein the titanium-containing molecular sieve is a molecular sieve having a mole ratio greater than about 15 of (1) silicon oxide to (2) titanium oxide and having, after calcination, the X-ray diffraction lines of Table II.

The present invention also provides a catalytic oxidation process comprising contacting under oxidation conditions (1) a reactant which is catalytically oxidizable in the presence of hydrogen peroxide, (2) aqueous hydrogen peroxide and (3) a catalytically effective amount of an oxidation catalyst comprising a molecular sieve having a mole ratio greater than about 15 of (1) silicon oxide to (2) titanium oxide and having, after calcination, the X-ray diffraction lines of Table II.

The present invention also provides a process for the epoxidation of an olefin comprising contacting said olefin with hydrogen peroxide in the presence of a catalytically effective amount of a catalyst comprising a molecular sieve having a mole ratio greater than about 15 of (1) silicon oxide to (2) titanium oxide and having, after calcination, the X-ray diffraction lines of Table II.

DETAILED DESCRIPTION OF THE INVENTION

Figure 1:
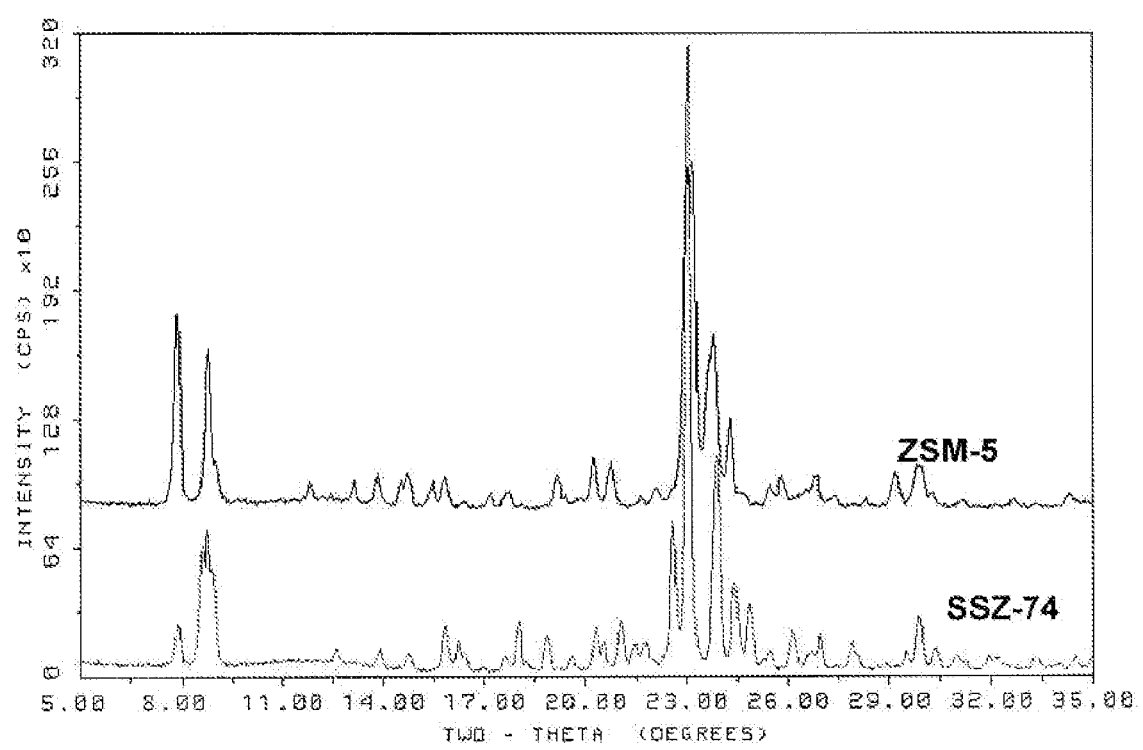
FIG. 1 shows a comparison of two X-ray diffraction patterns, the top one being ZSM-5 and the bottom one being SSZ-74.

The present invention comprises a molecular sieve designated herein "molecular sieve SSZ-74" or simply "SSZ-74".

In preparing SSZ-74, a hexamethylene-1,6-bis-(N-methyl-N-pyrrolidinium) dication is used as a structure directing agent ("SDA"), also known as a crystallization template. The SDA useful for making SSZ-74 has the following structure:

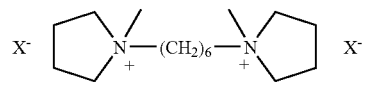

Hexamethylene-1,6-bis-(N-methyl-N-pyrrolidinium) dication

The SDA dication is associated with anions ($X^-$) which may be any anion that is not detrimental to the formation of the SSZ-74. Representative anions include halogen, e.g., fluoride, chloride, bromide and iodide, hydroxide, acetate, sulfate, tetrafluoroborate, carboxylate, and the like. Hydroxide is the most preferred anion. The structure directing agent (SDA) may be used to provide hydroxide ion. Thus, it is beneficial to ion exchange, for example, a halide to hydroxide ion.

In general, SSZ-74 is prepared by contacting (1) an active source(s) of silicon oxide, and (2) an active source(s) of titanium oxide with the hexamethylene 1,6-bis(N-methyl-N-pyrrolidinium)dication SDA in the presence of fluoride ion.

SSZ-74 is prepared from a reaction mixture comprising, in terms of mole ratios, the following:

TABLE A

| | Reaction Mixture | |
|---|---|---|
| | Typical | Preferred |
| $SiO_2/TiO_2$ | 100 and greater | |
| $OH^-/SiO_2$ | 0.20-0.80 | 0.40-0.60 |
| $Q/SiO_2$ | 0.20-0.80 | 0.40-0.60 |
| $M_{2/n}/SiO_2$ | 0-0.04 | 0-0.025 |
| $H_2O/SiO_2$ | 2-10 | 3-7 |
| $HF/SiO_2$ | 0.20-0.80 | 0.30-0.60 | where M is an alkali metal cation, alkaline earth metal cation or mixtures thereof; n is the valence of M (i.e., 1 or 2); Q is a hexamethylene-1,6-bis-(N-22 methyl-N-pyrrolidinium)dication and F is fluoride.

As noted above, the $SiO_2/X_aO_b$ mole ratio in the reaction mixture is 100 and greater. However, for the SSZ-74 to be effective in catalyzing the partial oxidation reactions, it must contain a catalytically effective amount of $TiO_2$.

A preferred source of silicon oxide is tetraethyl orthosilicate. A preferred source of titanium are tetraalkylorthotitanates.

In practice, SSZ-74 is prepared by a process comprising:

(a) preparing an aqueous solution containing (1) a source(s) of silicon oxide, (2) a source(s) of titanium oxide (3) a source of fluoride ion and (4) a hexamethylene-1,6-bis-(N-methyl-N-pyrrolidinium)dication having an anionic counterion which is not detrimental to the formation of SSZ-74;

(b) maintaining the aqueous solution under conditions sufficient to form crystals of SSZ-74; and (c) recovering the crystals of SSZ-74.

The reaction mixture is maintained at an elevated temperatures until the crystals of the SSZ-74 are formed. The hydrothermal crystallization is usually conducted under autogenous pressure, at a temperature between 100° C. and 200° C., preferably between 135° C. and 180° C. The crystallization period is typically greater than 1 day and preferably from about 3 days to about 20 days. The molecular sieve may be prepared using mild stirring or agitation.

During the hydrothermal crystallization step, the SSZ-74 crystals can be allowed to nucleate spontaneously from the reaction mixture. The use of SSZ-74 crystals as seed material can be advantageous in decreasing the time necessary for complete crystallization to occur. In addition, seeding can lead to an increased purity of the product obtained by promoting the nucleation and/or formation of SSZ-74 over any undesired phases. When used as seeds, SSZ-74 crystals are added in an amount between 0.1 and 10% of the weight of the first tetravalent element oxide, e.g. silica, used in the reaction mixture.

Once the molecular sieve crystals have formed, the solid product is separated from the reaction mixture by standard mechanical separation techniques such as filtration. The crystals are water-washed and then dried, e.g., at 90° C. to 150° C. for from 8 to 24 hours, to obtain the as-synthesized SSZ-74 crystals. The drying step can be performed at atmospheric pressure or under vacuum.

SSZ-74 as prepared has the X-ray diffraction lines of Table I below. SSZ-74 has a compositions, as synthesized (i.e., prior to removal of the SDA from the SSZ-74) and in the anhydrous state, comprising the following (in terms of mole ratios):

| | |
|---|---|
| $SiO_2/TiO_2$ | greater than 100 |
| $M_{2/n}/SiO_2$ | 0-0.03 |
| $Q/SiO_2$ | 0.30-0.70 |
| $F/SiO_2$ | 0.30-0.70 | wherein M is an alkali metal cation, alkaline earth metal cation or mixtures thereof; n is the valence of M (i.e., 1 or 2); Q is a hexamethylene-1,6-bis-(N-methyl-N-pyrrolidinium) dication and F is fluoride.

SSZ-74 is characterized by its X-ray diffraction pattern. SSZ-74, as-synthesized, has a crystalline structure whose X-ray powder diffraction pattern exhibits the characteristic lines shown in Table I.

TABLE I

As-Synthesized SSZ-74

| 2 Theta[a] | d-spacing (Angstroms) | Relative Integrated Intensity (%)[b] |
|---|---|---|
| 7.95 | 11.11 | W |
| 8.68 | 10.18 | M |
| 8.85 | 9.98 | W-M |
| 9.02 | 9.80 | W |
| 22.69 | 3.92 | W-M |
| 23.14 | 3.84 | VS |
| 24.01 | 3.70 | M |
| 24.52 | 3.63 | W |
| 24.93 | 3.57 | W |
| 29.95 | 2.98 | W |

[a] ±0.1
[b] The X-ray patterns provided are based on a relative intensity scale in which the strongest line in the X-ray pattern is assigned a value of 100; W (weak) is less than 20; M (medium) is between 20 and 40; S (strong) is between 40 and 60; VS (very strong) is greater than 60.

Table IA below shows the X-ray powder diffraction lines for as-synthesized SSZ-74 including actual relative intensities.

TABLE IA

As-Synthesized SSZ-74

| 2 Theta[a] | d-spacing (Angstroms) | Intensity |
|---|---|---|
| 7.95 | 11.11 | 7.9 |
| 8.68 | 10.18 | 21.1 |
| 8.65 | 9.98 | 18.7 |
| 9.02 | 9.80 | 11.3 |
| 11.30 | 7.82 | 0.4 |
| 12.70 | 6.96 | 1.8 |
| 13.98 | 6.33 | 2.4 |
| 14.77 | 5.99 | 0.5 |
| 14.85 | 5.96 | 2.1 |
| 15.93 | 5.56 | 6.3 |
| 16.30 | 5.43 | 4.6 |
| 16.50 | 5.37 | 1.8 |
| 17.05 | 5.20 | 0.8 |
| 17.41 | 5.09 | 0.1 |
| 17.11 | 5.00 | 2.0 |
| 18.09 | 4.90 | 7.4 |
| 18.38 | 4.82 | 0.7 |
| 18.89 | 4.69 | 0.9 |
| 18.96 | 4.68 | 4.4 |
| 19.69 | 4.51 | 1.8 |
| 20.39 | 4.35 | 5.1 |
| 20.63 | 4.30 | 4.2 |
| 21.12 | 4.20 | 7.1 |
| 21.55 | 4.12 | 5.4 |
| 21.75 | 4.08 | 0.5 |
| 21.80 | 4.07 | 1.4 |
| 21.88 | 4.06 | 2.1 |
| 21.96 | 4.04 | 1.5 |
| 22.17 | 4.01 | 0.8 |
| 22.69 | 3.92 | 18.9 |
| 23.14 | 3.84 | 100.0 |
| 23.89 | 3.72 | 9.4 |
| 24.01 | 3.70 | 25.6 |
| 24.52 | 3.63 | 13.7 |
| 24.68 | 3.60 | 2.1 |
| 24.93 | 3.57 | 11.3 |
| 25.09 | 3.55 | 0.9 |
| 25.37 | 3.51 | 1.7 |
| 25.57 | 3.48 | 2.7 |
| 26.20 | 3.40 | 5.5 |
| 26.31 | 3.38 | 0.8 |
| 26.67 | 3.34 | 2.0 |
| 26.76 | 3.33 | 1.0 |
| 26.82 | 3.32 | 0.9 |
| 27.01 | 3.30 | 3.4 |
| 27.05 | 3.29 | 0.8 |

TABLE IA-continued

As-Synthesized SSZ-74

| 2 Theta[a] | d-spacing (Angstroms) | Intensity |
|---|---|---|
| 27.48 | 3.24 | 0.8 |
| 27.99 | 3.19 | 4.2 |
| 28.18 | 3.16 | 0.8 |
| 28.78 | 3.10 | 0.6 |
| 29.03 | 3.07 | 0.7 |
| 29.31 | 3.04 | 0.9 |
| 29.58 | 3.02 | 2.4 |
| 29.95 | 2.98 | 9.6 |
| 30.44 | 2.93 | 3.7 |
| 31.09 | 2.87 | 3.1 |
| 31.36 | 2.85 | 0.8 |
| 31.98 | 2.80 | 2.2 |
| 32.23 | 2.78 | 1.7 |
| 32.37 | 2.76 | 0.6 |
| 32.64 | 2.74 | 1.5 |
| 33.03 | 2.71 | 0.1 |
| 33.34 | 2.69 | 1.0 |
| 33.47 | 2.68 | 1.3 |
| 34.08 | 2.63 | 0.7 |
| 34.55 | 2.59 | 1.8 |
| 34.73 | 2.58 | 0.4 |

[a]±0.1

After calcination, the X-ray powder diffraction pattern for SSZ-74 exhibits the characteristic lines shown in Table II below.

TABLE II

Calcined SSZ-74

| 2 Theta[a] | d-spacing (Angstroms) | Relative Integrated Intensity (%) |
|---|---|---|
| 7.98 | 11.07 | M |
| 8.70 | 10.16 | VS |
| 8.89 | 9.93 | S |
| 9.08 | 9.74 | S |
| 14.02 | 6.31 | W |
| 14.93 | 5.93 | M |
| 16.03 | 5.52 | M |
| 23.26 | 3.82 | VS |
| 23.95 | 3.71 | W |
| 24.08 | 3.69 | M |

[a]±0.1

Table IIA below shows the X-ray powder diffraction lines for calcined SSZ74 including actual relative intensities.

TABLE IIA

Calcined SSZ-74

| 2 Theta[a] | d-spacing (Angstroms) | Relative Integrated Intensity (%) |
|---|---|---|
| 7.98 | 11.07 | 34.9 |
| 8.70 | 10.16 | 86.8 |
| 8.89 | 9.93 | 40.2 |
| 9.08 | 9.74 | 47.0 |
| 9.66 | 9.15 | 1.0 |
| 11.26 | 7.85 | 0.4 |
| 11.34 | 7.80 | 0.5 |
| 12.76 | 6.93 | 1.1 |
| 13.26 | 6.67 | 4.6 |
| 14.02 | 6.31 | 13.4 |
| 14.93 | 5.93 | 20.9 |
| 16.03 | 5.52 | 23.5 |
| 16.39 | 5.40 | 4.3 |
| 16.61 | 5.33 | 4.4 |
| 17.12 | 5.18 | 3.0 |

TABLE IIA-continued

Calcined SSZ-74

| 2 Theta[a] | d-spacing (Angstroms) | Relative Integrated Intensity (%) |
|---|---|---|
| 17.80 | 4.98 | 2.8 |
| 18.19 | 4.87 | 7.6 |
| 19.05 | 4.66 | 1.9 |
| 19.74 | 4.49 | 0.4 |
| 20.44 | 4.34 | 3.0 |
| 20.75 | 4.28 | 3.4 |
| 21.19 | 4.19 | 7.7 |
| 21.67 | 4.10 | 4.1 |
| 21.99 | 4.04 | 5.8 |
| 22.68 | 3.92 | 3.7 |
| 22.79 | 3.90 | 9.5 |
| 23.26 | 3.82 | 100.0 |
| 23.95 | 3.71 | 14.2 |

[a]±0.1

The X-ray powder diffraction patterns were determined by standard techniques. The radiation was the K-alpha/doublet of copper. The peak heights and the positions, as a function of 2θ where θ is the Bragg angle, were read from the relative intensities of the peaks, and d, the interplanar spacing in Angstroms corresponding to the recorded lines, can be calculated.

The variation in the scattering angle (two theta) measurements, due to instrument error and to differences between individual samples, is estimated at ±0.1 degrees.

Representative peaks from the X-ray diffraction pattern of calcined SSZ-74 are shown in Table II. Calcination can result in changes in the intensities of the peaks as compared to patterns of the "as-made" material as well as minor shifts in the diffraction pattern.

Crystalline SSZ-74 can be used as synthesized, but preferably will be thermally treated (calcined). Usually, it is desirable to remove the alkali metal cation (if any) by ion exchange and replace it with hydrogen, ammonium, or any desired metal ion.

SSZ-74 can be formed into a wide variety of physical shapes. Generally speaking, the molecular sieve can be in the form of a powder, a granule, or a molded product, such as extrudate having a particle size sufficient to pass through a 2-mesh (Tyler) screen and be retained on a 400-mesh (Tyler) screen. In cases where the catalyst is molded, such as by extrusion with an organic binder, the SSZ-74 can be extruded before drying, or, dried or partially dried and then extruded.

SSZ-74 can be composited with other materials resistant to the temperatures and other conditions employed in organic conversion processes. Such matrix materials include active and inactive materials and synthetic or naturally occurring zeolites as well as inorganic materials such as clays, silica and metal oxides. Examples of such materials and the manner in which they can be used are disclosed in U.S. Pat. No. 4,910,006, issued May 20, 1990 to Zones et al., and U.S. Pat. No. 5,316,753, issued May 31, 1994 to Nakagawa, both of which are incorporated by reference herein in their entirety.

The partial oxidation of low value hydrocarbons such as alkanes and alkenes into high value products such as alcohols and epoxides is of great commercial interest. These oxidation products are not only valuable as is, but also as intermediates for specialty chemicals including pharmaceuticals and pesticides.

U.S. Pat. No. 4,410,501, issued Oct. 18, 1983 to Esposito et al., discloses a titanium-containing analogue of the all-silica ZSM-5 molecular sieve. This material (known as "TS-1") has been found to be useful in catalyzing a wide range of partial oxidation chemistries, for example the production of catechol and hydroquinone from phenol and hydrogen peroxide ($H_2O_2$) and the manufacture of propylene oxide and cyclohexanone oxime from propylene and cyclohexanone, respectively. In addition, TS-1 can be used to catalyze the reaction of alkanes and aqueous $H_2O_2$ to form alcohols and ketones. (See Huybrechts, D.R.C. et al., *Nature* 1990, 345, 240-2402 and Tatsumi, T. et al., *J.C.S. Chem. Commun.* 1990, 476-477.)

TS-1 has many salient features, other than its catalytic abilities, which make it attractive as a commercial catalyst. Most importantly, it is a solid. This allows for easy separation from the reactants and products (typically liquids) by simple, inexpensive filtration. Moreover, this solid has high thermal stability and a very long lifetime. Calcination in air at moderate temperatures (550° C.) restores the material to its original catalytic ability. TS-1 performs best at mild temperatures (<100° C.) and pressures (1 atm). The oxidant used for reactions catalyzed by TS-1 is aqueous $H_2O_2$, which is important because aqueous $H_2O_2$ is relatively inexpensive and its by-product is water. Hence, the choice of oxidant is favorable from both a commercial and environmental point of view.

While a catalyst system based on TS-1 has many useful features, it has one serious drawback. The zeolite structure of TS-1 includes a regular system of pores which are formed by nearly circular rings of ten silicon atoms (called 10-membered rings, or simply "10 rings") creating pore diameters of approximately 5.5 Å. This small size results in the exclusion of molecules larger than 5.5 Å. Because the catalytically active sites are located within the pores of the zeolite, any exclusion of molecules from the pores results in poor catalytic activity.

SSZ-74 containing titanium oxide (Ti-SSZ-74) is useful as a catalyst in oxidation reactions, particularly in the oxidation of hydrocarbons. Examples of such reactions include, but are not limited to, the epoxidation olefins, the oxidation of alkanes, and the oxidation of sulfur-containing, nitrogen-containing or phosphorus-containing compounds.

The amount of Ti-SSZ-74 catalyst employed is not critical, but should be sufficient so as to substantially accomplish the desired oxidation reaction in a practicably short period of time (i.e., a catalytically effective amount). The optimum quantity of catalyst will depend upon a number of factors including reaction temperature, the reactivity and concentration of the substrate, hydrogen peroxide concentration, type and concentration of organic solvent, as well as the activity of the catalyst. Typically, however, the amount of catalyst will be from about 0.001 to 10 grams per mole of substrate.

Typically, the Ti-SSZ-74 is thermally treated (calcined) prior to use as a catalyst.

The oxidizing agent employed in the oxidation processes of this invention is a hydrogen peroxide source such as hydrogen peroxide ($H_2O_2$) or a hydrogen peroxide precursor (i.e., a compound which under the oxidation reaction conditions is capable of generating or liberating hydrogen peroxide).

The amount of hydrogen peroxide relative to the amount of substrate is not critical, but must be sufficient to cause oxidation of at least some of the substrate. Typically, the molar ratio of hydrogen peroxide to substrate is from about 100:1 to about 1:100, preferably 10:1 to about 1:0. When the substrate is an olefin containing more than one carbon-carbon double bond, additional hydrogen peroxide may be required. Theoretically, one equivalent of hydrogen peroxide is required to oxidize one equivalent of a mono-unsaturated substrate, but it may be desirable to employ an excess of one reactant to optimize selectivity to the epoxide. In particular, the use of a moderate to large excess (e.g., 50 to 200%) of olefin relative to hydrogen peroxide may be advantageous for certain substrates.

If desired, a solvent may additionally be present during the oxidation reaction in order to dissolve the reactants other than the Ti-SSZ-74, to provide better temperature control, or to favorably influence the oxidation rates and selectivities. The solvent, if present, may comprise from 1 to 99 weight percent of the total oxidation reaction mixture and is preferably selected such that it is a liquid at the oxidation reaction temperature. Organic compounds having boiling points at atmospheric pressure of from about 50° C. to about 150° C. are generally preferred for use. Excess hydrocarbon may serve as a solvent or diluent. Illustrative examples of other suitable solvents, include, but are not limited to, ketones (e.g., acetone, methyl ethyl ketone, acetophenone), ethers (e.g., tetrahydrofuran, butyl ether), nitriles (e.g., acetonitrile), aliphatic and aromatic hydrocarbons, halogenated hydrocarbons, and alcohols (e.g., methanol, ethanol, isopropyl alcohol, t-butyl alcohol, alpha-methyl benzyl alcohol, cyclohexanol). More than one type of solvent may be utilized. Water may also be employed as a solvent or diluent.

The reaction temperature is not critical, but should be sufficient to accomplish substantial conversion of the substrate within a reasonably short period of time. It is generally advantageous to carry out the reaction to achieve as high a hydrogen peroxide conversion as possible, preferably at least about 50%, more preferably at least about 90%, most preferably at least about 95%, consistent with reasonable selectivities. The optimum reaction temperature will be influenced by catalyst activity, substrate reactivity, reactant concentrations, and type of solvent employed, among other factors, but typically will be in a range of from about 0° C. to about 150° C. (more preferably from about 25° C. to about 120° C.). Reaction or residence times from about one minute to about 48 hours (more desirably from about ten minutes to about eight hours) will typically be appropriate, depending upon the above-identified variables. Although subatmospheric pressures can be employed, the reaction is preferably performed at atmospheric or at elevated pressure (typically, between one and 100 atmospheres), especially when the boiling point of the substrate is below the oxidation reaction temperature. Generally, it is desirable to pressurize the reaction vessel sufficiently to maintain the reaction components as a liquid phase mixture. Most (over 50%) of the substrate should preferably be present in the liquid phase.

The oxidation process of this invention may be carried out in a batch, continuous, or semi-continuous manner using any appropriate type of reaction vessel or apparatus such as a fixed bed, transport bed, fluidized bed, stirred slurry, or CSTR reactor. The reactants may be combined all at once or sequentially. For example, the hydrogen peroxide or hydrogen peroxide precursor may be added incrementally to the reaction zone. The hydrogen peroxide could also be generated in situ within the same reactor zone where oxidation is taking place.

Once the oxidation has been carried out to the desired degree of conversion, the oxidized product may be separated and recovered from the reaction mixture using any appropriate technique such as fractional distillation, extractive distillation, liquid-liquid extraction, crystallization, or the like.

Olefin Epoxidation

One of the oxidation reactions for which Ti-SSZ-74 is useful as a catalyst is the epoxidation of olefins, The olefin substrate epoxidized in the process of this invention may be any organic compound having at least one ethylenically unsaturated functional group (i.e., a carbon-carbon double bond) and may be a cyclic, branched or straight-chain olefin. The olefin may contain aryl groups (e.g., phenyl, naphthyl). Preferably, the olefin is aliphatic in character and contains from 2 to about 20 carbon atoms. The use of light (low-boiling) $C_2$ to $C_{10}$ mono-olefins is especially advantageous.

More than one carbon-carbon double bond may be present in the olefin, i.e., dienes, trienes and other polyunsaturated substrates may be used. The double bond may be in a terminal or internal position in the olefin or may alternatively form part of a cyclic structure (as in cyclooctene, for example).

Other examples of suitable substrates include unsaturated fatty acids or fatty acid derivatives such as esters.

The olefin may contain substituents other than hydrocarbon substituents such as halide, carboxylic acid, ether, hydroxy, thiol, nitro, cyano, ketone, acyl, ester, anhydride, amino, and the like.

Exemplary olefins suitable for use in the process of this invention include ethylene, propylene, the butenes (i.e. 1,2-butene, 2,3-butene, isobutylene), butadiene, the pentenes, isoprene, 1-hexene, 3-hexene, 1-heptene, 1-octene, diisobutylene, 1-nonene, 1-tetradecene, pentamyrcene, camphene, 1-undecene, 1-dodecene, 1-tridecene, 1-tetradecene, 1-pentadecene, 1-hexadecene, 1-heptadecene, 1-octadecene, 1-nonadecene, 1-eicosene, the trimers and tetramers of propylene, cyclopentene, a cyclohexene, cycloheptene, cyclooctene, cyclooctadiene, dicyclopentadiene, methylenecyclopropane, methylenecyclopentane, methylenecyclohexane, vinyl cyclohexane, vinyl cyclohexene, methallyl ketone, allyl chloride, the dichlorobutenes, allyl alcohol, allyl carbonate, allyl acetate alkyl acrylates and methacrylates, diallyl maleate, diallyl phthalate, and unsaturated fatty acids, such as oleic acid, linolenic acid, linoleic acid, erucic acid, palmitolec acid, and ricinoleic acid and their esters (including mono-, di-, and triglyceride is esters) and the like.

Olefins which are especially useful for epoxidation are the $C_2$-$C_{20}$ olefins having the general structure

wherein $R^3$, $R^4$, $R^5$ and $R^6$ are the same or different and are selected from the group consisting of hydrogen and $C_1$-$C_-$alkyl.

Mixtures of olefins may be epoxidized and the resulting mixtures of epoxides either employed in the mixed form or separated into the different component epoxides.

The present invention further provides a process for oxidation of hydrocarbons comprising contacting said hydrocarbon with hydrogen peroxide in the presence of a catalytically effective amount of Ti-SSZ-74 for a time and at a temperature effective to oxidize said hydrocarbon.

EXAMPLES

The following examples demonstrate but do not limit the present invention.

Example 1

Synthesis of Hexamethylene-1,6-bis-(N-methyl-N-pyrrolidinium)dication SDA

In 50 ml of acetone was dissolved 5 ml (48 mmoles) of N-methyl pyrrolidine. 4.9 Grams of 1,6 dibromohexane (20 mmoles) were added and the resulting mixture was stirred at room temperature for three days. Solids formed and were collected by filtration and washed with ether and kept in a vacuum oven. Then 3.71 grams of the dried solid was mixed into 18.7 grams of water and 9.57 grams of AG1-X8 resin for exchange to the OH form. The exchange was run overnight and then the solution was collected and titrated.

Example 2

Synthesis of All-Silica SSZ74

6.4 Grams of the solution from Example 1 (3 mmoles) was mixed in a tared Teflon cup with 1.26 grams of tetraethyl orthosilicate and then allowed to evaporate (in a hood) for several days as hydrolysis occurred. A second reaction was set up the same way. After evaporation to the appearance of dryness, one reaction was given 0.20 gram of water and mixed. The second was given 0.60 gram of water and the same treatment ensued. 0.125 Gram of about 50% HF was carefully added to each reaction mixture and the contents were stirred with a plastic spatula and a thick gel formed. In the first case the H2O/SiO2 ratio was now roughly 3.5 and it was 7.0 in the second case. The materials were heated to 150° C. and at 43 RPM in tumbled Parr reactors placed in a Blue M convection heating oven. The reactions were cooled and opened in 6 day periods with a small amount examined by Scanning Electron Microscopy to determine if crystals had formed. After 22 days there was crystalline material in both and the solids were collected (filtration) and washed with copious amounts of water, air dried and then examined by X-ray diffraction (XRD). The product in both cases was SSZ-74.

Example 3

Calcination of SSZ-74

The products from both reactions in Example 2 were calcined in stages and in air to 595° C. to remove the organic content. The materials were found to be stable and the XRD patterns showed the relationship to the as-made SSZ-74.

Example 4

Adsorption of 2.2-Dimethylbutane

The calcined material of Example 3 was then tested for the uptake of the hydrocarbon 2,2-dimethylbutane. This adsorbate does not enter small pore zeolites (8-ring portals) and sometimes is hindered in entering intermediate pore zeolites like ZSM-5. The SSZ-74 showed a profile more characteristic of intermediate pore materials (as contrasted to Y zeolite, a large pore material), showing steady gradual uptake of the adsorbate.

SSZ-74 was shown to adsorb about 0.08 cc/gram after 3 hours of exposure to the 2,2 dimethyl butane adsorbate using a pulsed mode. This value compares with an analysis for ZSM-5 zeolite which gives a value closer to 0.07 cc/gm at the same point in time under the same experimental conditions. This would indicate that the pores of SSZ-74 are at least 10-rings Example 5

Synthesis of Aluminosilicate SSZ-74

The synthesis parameters of Example 2 were repeated except for the following changes. (1) 0.04 gram of Y zeolite material LZ-210 was added as a potential contributor of Al; (2) the initial H2O/SiO2 ratio for the synthesis was adjusted to 5; (3) seeds of a successful SSZ-74 product were added;

and (4) the reaction was run at 170° C. After 9 days there was crystalline material which was SSZ-74 when worked up and analyzed by XRD. The solids were calcined then as in Example 3.

Example 6

Constraint Index 0.12 grams of the material from Example 5, in a 20-40 pelleted and meshed range, was loaded into a stainless steel reactor and run in a Constraint Index test (50/50 n-hexane/3-methylpentane). The normal feed rate was used (8 µl/min.) and the test was run at 700° F. after the catalyst had been dried in the reactor to near 1000° F. Helium flow was used. At 10 minutes on-stream nearly 30% of the feed was being converted with about equal amounts of each reactant. The selectivity did not change as the catalyst fouled to half the conversion at 100 minutes. The pores of the active SSZ-74 were at least intermediate in size.

Example 7

Synthesis of Aluminosilicate SSZ-74

Three mMoles of SDA solution and 1.26 grams (6 mMoles) of tetraethylorthosilicate were combined in a Teflon cup for a Parr reactor. The contents were allowed to react and then most of the water and then the ethanol by-product were allowed to evaporate in a hood over several days. Once the $H_2O/SiO_2$ ratio was about 5, from the evaporation, 0.04 grams of LZ-210 zeolite were added (LZ-210 is a Y zeolite which has been treated with $(NH_4^+)_2SiF_6$ to provide some de-alumination). A few mg of seeds of SSZ-74 were added in the as-made state. Lastly, 0.132 gram of 50% HF was added and the reactor was closed up and heated at 170° C., 43 RPM, for six days. A sample of the cooled reaction product showed nicely crystalline material in an electron microscope. The reaction contents were worked up and dried.

Analysis by X-ray diffraction showed the product to be molecular sieve SSZ-74.

The sample was calcined (In air to 595° C.) and then pelleted and meshed (20-40) and run in a standard Constraint Index test, At 700° F. the initial conversion was 28% with a CI value of 1.1. With time-on-stream the catalyst showed a steady deactivation while the CI value did not change much.

What is claimed is:

1. A process for oxidation of hydrocarbons comprising contacting said hydrocarbon with an oxidizing agent in the presence of a catalytically effective amount of a titanium-containing molecular sieve for a time and at a temperature effective to oxidize said hydrocarbon, wherein the titanium-containing molecular sieve is a molecular sieve having a mole ratio greater than about 15 of (1) silicon oxide to (2) titanium oxide and having, after calcination, the X-ray diffraction lines of Table II, as follows:

TABLE II

Calcined SSZ-74

| 2 Theta[a] | d-spacing (Angstroms) | Relative Integrated Intensity (%) |
|---|---|---|
| 7.98 | 11.07 | M |
| 8.70 | 10.16 | VS |
| 8.89 | 9.93 | S |
| 9.08 | 9.74 | S |
| 14.02 | 6.31 | W |
| 14.93 | 5.93 | M |
| 16.03 | 5.52 | M |
| 23.26 | 3.82 | VS |
| 23.95 | 3.71 | W |
| 24.08 | 3.69 | M. |

[a] ±0.1

2. A process for epoxidation of an olefin comprising contacting said olefin with hydrogen peroxide in the presence of a catalytically effective amount of a titanium-containing molecular sieve for a time and at a temperature effective to epoxidize said olefin, wherein the titanium-containing molecular sieve is a molecular sieve having a mole ratio greater than about 15 of (1) silicon oxide to (2) titanium oxide and having, after calcination, the X-ray diffraction lines of Table II, as follows:

TABLE II

Calcined SSZ-74

| 2 Theta[a] | d-spacing (Angstroms) | Relative Integrated Intensity (%) |
|---|---|---|
| 7.98 | 11.07 | M |
| 8.70 | 10.16 | VS |
| 8.89 | 9.93 | S |
| 9.08 | 9.74 | S |
| 14.02 | 6.31 | W |
| 14.93 | 5.93 | M |
| 16.03 | 5.52 | M |
| 23.26 | 3.82 | VS |
| 23.95 | 3.71 | W |
| 24.08 | 3.69 | M. |

[a] ±0.1

3. A process for oxidizing cyclohexane comprising contacting said cyclohexane with hydrogen peroxide in the presence of a catalytically effective amount of a titanium-containing molecular sieve for a time and at a temperature effective to oxidize said cyclohexane, wherein the titanium-containing molecular sieve is a molecular sieve having a mole ratio greater than about 15 of (1)silicon oxide to (2) titanium oxide and having, after calcination, the X-ray diffraction lines of Table 11, as follows:

TABLE II

Calcined SSZ-74

| 2 Theta[a] | d-spacing (Angstroms) | Relative Integrated Intensity (%) |
|---|---|---|
| 7.98 | 11.07 | M |
| 8.70 | 10.16 | VS |
| 8.89 | 9.93 | S |
| 9.08 | 9.74 | S |
| 14.02 | 6.31 | W |
| 14.93 | 5.93 | M |
| 16.03 | 5.52 | M |
| 23.26 | 3.82 | VS |
| 23.95 | 3.71 | W |
| 24.08 | 3.69 | M. |

[a] ±0.1

4. A catalytic oxidation process comprising contacting under oxidation conditions (1) a reactant which is catalytically oxidizable in the presence of hydrogen peroxide, (2) aqueous hydrogen peroxide and (3) a catalytically effective amount of an oxidation catalyst comprising a molecular sieve having a mole ratio greater than about 15 of (1) silicon oxide to (2) titanium oxide and having, after calcination, the X-ray diffraction lines of Table II, as follows;

TABLE II

Calcined SSZ-74

| 2 Theta[a] | d-spacing (Angstroms) | Relative Integrated Intensity (%) |
|---|---|---|
| 7.98 | 11.07 | M |
| 8.70 | 10.16 | VS |
| 8.89 | 9.93 | S |
| 9.08 | 9.74 | S |
| 14.02 | 6.31 | W |
| 14.93 | 5.93 | M |
| 16.03 | 5.52 | M |
| 23.26 | 3.82 | VS |
| 23.95 | 3.71 | W |
| 24.08 | 3.69 | M. |

[a] ±0.1

5. The process of claim 4 wherein the oxidizable reactant is a hydrocarbon.

6. A process for the epoxidation of an olefin comprising contacting said olefin with hydrogen peroxide in the presence of a catalytically effective amount of a catalyst comprising a molecular sieve having a mole ratio greater than about 15 of (1) silicon oxide to (2) titanium oxide and having, after calcination, the X-ray diffraction lines of Table II, as follows:

TABLE II

Calcined SSZ-74

| 2 Theta[a] | d-spacing (Angstroms) | Relative Integrated Intensity (%) |
|---|---|---|
| 7.98 | 11.07 | M |
| 8.70 | 10.16 | VS |
| 8.89 | 9.93 | S |
| 9.08 | 9.74 | S |
| 14.02 | 6.31 | W |
| 14.93 | 5.93 | M |
| 16.03 | 5.52 | M |
| 23.26 | 3.82 | VS |
| 23.95 | 3.71 | W |
| 24.08 | 3.69 | M. |

[a] ±0.1

* * * * *